United States Patent
Meza-Romero et al.

(10) Patent No.: US 10,689,446 B2
(45) Date of Patent: Jun. 23, 2020

(54) RECOMBINANT CD74 POLYPEPTIDES

(71) Applicants: Oregon Health & Science University, Portland, OR (US); The United States Government as represented by The Department of Veterans Affairs, Washington, DC (US)

(72) Inventors: Roberto Meza-Romero, Beaverton, OR (US); Gil Benedek, Portland, OR (US); Arthur A. Vandenbark, Portland, OR (US)

(73) Assignees: OREGON HEALTH & SCIENCE UNIVERSITY, Portland, OR (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 269 days.

(21) Appl. No.: 15/629,573

(22) Filed: Jun. 21, 2017

(65) Prior Publication Data
US 2017/0369577 A1    Dec. 28, 2017

Related U.S. Application Data

(60) Provisional application No. 62/353,497, filed on Jun. 22, 2016.

(51) Int. Cl.
*C07K 14/74* (2006.01)
*C07K 14/705* (2006.01)
*C07K 16/28* (2006.01)

(52) U.S. Cl.
CPC .... *C07K 16/2833* (2013.01); *C07K 14/70539* (2013.01); *C07K 2319/40* (2013.01)

(58) Field of Classification Search
None
See application file for complete search history.

(56) References Cited

U.S. PATENT DOCUMENTS 8,999,984 B2 * 4/2015 Mitchell .............. A61K 31/513
514/247
2017/0114117 A1 4/2017 Vandenbark et al.

OTHER PUBLICATIONS

Leng et al (J. Exp. Med. 2003,197(11): 1467-1476) (Year: 2003).*
ThermoFisher Scientific 2019 (Year: 2019).*
Gil-Yarom et al (2014, Atlas of Genetics and Cytogenetics in Oncology and Haematology, 14 pages) (Year: 2014).*
Leng et al., "MIF Signal Transduction Initiated by Binding to CD74," *J. Exp. Med.* vol. 197, No. 11, pp. 1467-1476, 2003.
Meza-Romero et al., "Modeling of both shared and distinct interactions between MIF and its homologue D-DT with their common receptor CD74," *Cytokine*, vol. 88, pp. 62-70, 2016.
Meza-Romero et al., "Predicted structure of MIF/CD74 and RTL1000/CD74 complexes," *Metab Brain Dis*, vol. 31, pp. 249-255, 2016.

* cited by examiner

*Primary Examiner* — G. R. Ewoldt
*Assistant Examiner* — Marianne DiBrinno
(74) *Attorney, Agent, or Firm* — Ballard Spahr LLP (57) ABSTRACT

Disclosed are recombinant CD74 polypeptides mutated relative to the naturally occurring CD74 polypeptides with improved properties such as binding of CD74 ligands such as MIF and RTL1000 as well as polynucleotides that encode the polypeptides, expression vectors comprising the polynucleotides, bacteria that include the expression vectors, and methods of making the recombinant polypeptides.

3 Claims, 7 Drawing Sheets
Specification includes a Sequence Listing.

SEQUENCE LISTING

<160> NUMBER OF SEQ ID NOS: 8

<210> SEQ ID NO 1
<211> LENGTH: 191
<212> TYPE: PRT
<213> ORGANISM: Artificial Sequence
<220> FEATURE:
<223> OTHER INFORMATION: chimeric protein

<400> SEQUENCE: 1

Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Val Thr Ser Gln Asn Leu Gln Leu Glu Asn Leu Arg Met Lys Leu
65                  70                  75                  80

Pro Lys Pro Pro Lys Pro Val Ser Lys Met Arg Met Ala Thr Pro Leu
                85                  90                  95

Leu Met Gln Ala Leu Pro Met Gly Ala Leu Pro Gln Gly Pro Met Gln
            100                 105                 110

Asn Ala Thr Lys Tyr Gly Asn Met Thr Glu Asp His Val Met His Leu
        115                 120                 125

Leu Gln Asn Ala Asp Pro Leu Lys Val Tyr Pro Pro Leu Lys Gly Ser
    130                 135                 140

Phe Pro Glu Asn Leu Arg His Leu Lys Asn Thr Met Glu Thr Ile Asp
145                 150                 155                 160

Trp Lys Val Phe Glu Ser Trp Met His His Trp Leu Leu Phe Glu Met
                165                 170                 175

Ser Arg His Ser Leu Glu Gln Lys Pro Thr Asp Ala Pro Pro Lys
            180                 185                 190

<210> SEQ ID NO 2
<211> LENGTH: 591
<212> TYPE: DNA
<213> ORGANISM: Artificial Sequence
<220> FEATURE:
<223> OTHER INFORMATION: codon optimized nucleic acid

<400> SEQUENCE: 2
ccggctagca tggatgacca acgcgacctc atctctaacc atgaacagtt gcccatactg      60
ggcaaccgcc ctagagagcc agaaaggtgc agccgtggag ctctgtacac cggtgtctct     120
gtcctggtgg ctctgctctt ggctgggcag gccaccactg cttacttcct gtaccagcag     180
cagggccggc tggacaaact gacagtcacc tcccagaacc tgcagctgga gaacctgcgc     240
atgaagcttc ccaagcctcc caagcctgtg agcaagatgc gcatggccac cccgctgctg     300
atgcaggcgc tgcccatggg agccctgccc caggggccca tgcagaatgc caccaagtat     360
ggcaacatga cagaggacca tgtgatgcac ctgctccaga atgctgaccc cctgaaggtg     420
tacccgccac tgaaggggag cttcccggag aacctgagac cttaagaa caccatggag      480 accatagact ggaaggtctt tgagagctgg atgcaccatt ggctcctgtt tgaaatgagc     540
aggcactcct tggagcaaaa gcccactgac gctccaccga aatgactcga g             591

<210> SEQ ID NO 3
<211> LENGTH: 191
<212> TYPE: PRT
<213> ORGANISM: Artificial Sequence
<220> FEATURE:
<223> OTHER INFORMATION: chimeric protein

<400> SEQUENCE: 3

```
Met Asp Asp Gln Arg Asp Leu Ile Ser Asn His Glu Gln Leu Pro Ile
1               5                   10                  15

Leu Gly Asn Arg Pro Arg Glu Pro Glu Arg Ser Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Val Thr Ser Gln Asn Leu Gln Leu Glu Asn Leu Arg Met Lys Leu
65                  70                  75                  80

Pro Lys Pro Pro Lys Pro Val Ser Lys Met Arg Met Ala Thr Pro Leu
                85                  90                  95

Leu Met Gln Ala Leu Pro Met Gly Ala Leu Pro Gln Gly Pro Met Gln
            100                 105                 110

Asn Ala Thr Lys Tyr Gly Asn Met Thr Glu Asp His Val Met His Leu
        115                 120                 125

Leu Gln Asn Ala Asp Pro Leu Lys Val Tyr Pro Pro Leu Lys Gly Ser
    130                 135                 140

Phe Pro Glu Asn Leu Arg His Leu Lys Asn Thr Met Glu Thr Ile Asp
145                 150                 155                 160

Trp Lys Val Phe Glu Ser Trp Met His His Trp Leu Leu Phe Glu Met
                165                 170                 175

Ser Arg His Ser Leu Glu Gln Lys Pro Thr Asp Ala Pro Pro Lys
            180                 185                 190
```

<210> SEQ ID NO 4
<211> LENGTH: 591
<212> TYPE: DNA
<213> ORGANISM: Artificial Sequence
<220> FEATURE:
<223> OTHER INFORMATION: codon optimized nucleic acid

<400> SEQUENCE: 4

```
ccggctagca tgatgacca acgcgacctc atctctaacc atgaacagtt gcccatactg      60
ggcaaccgcc ctagagagcc agaaaggagc agccgtggag ctctgtacac cggtgtctct    120
gtcctggtgg ctctgctctt ggctgggcag gccaccactg cttacttcct gtaccagcag    180
cagggccggc tggacaaact gacagtcacc tcccagaacc tgcagctgga aacctgcgc    240
atgaagcttc ccaagcctcc caagcctgtg agcaagatgc gcatggccac ccgctgctg    300
atgcaggcgc tgcccatggg agccctgccc caggggccca tgcagaatgc caccaagtat    360
ggcaacatga cagaggacca tgtgatgcac ctgctccaga atgctgaccc cctgaaggtg    420
tacccgccac tgaaggggag cttcccggag aacctgagac accttaagaa caccatggag    480
accatagact ggaaggtctt tgagagctgg atgcaccatt ggctcctgtt tgaaatgagc    540
aggcactcct tggagcaaaa gcccactgac gctccaccga aatgactcga g             591
```

<210> SEQ ID NO 5
<211> LENGTH: 194
<212> TYPE: PRT

<213> ORGANISM: Artificial Sequence
<220> FEATURE:
<223> OTHER INFORMATION: mutated protein

<400> SEQUENCE: 5

| | | | | | | | | | | | | | | |
|---|---|---|---|---|---|---|---|---|---|---|---|---|---|---|
| Met | Ala | Ser | Met | Asp | Asp | Gln | Arg | Asp | Leu | Ile | Ser | Asn | His | Glu | Gln |
| 1 | | | | 5 | | | | | 10 | | | | | 15 | |
| Leu | Pro | Ile | Leu | Gly | Asn | Arg | Pro | Arg | Glu | Pro | Glu | Arg | Ser | Ser | Arg |
| | | | 20 | | | | | 25 | | | | | 30 | | |
| Gly | Ala | Leu | Tyr | Thr | Gly | Val | Ser | Val | Leu | Val | Ala | Leu | Leu | Leu | Ala |
| | | 35 | | | | | 40 | | | | | 45 | | | |
| Gly | Gln | Ala | Thr | Thr | Ala | Tyr | Phe | Leu | Tyr | Gln | Gln | Gln | Gly | Arg | Leu |
| | 50 | | | | | 55 | | | | | 60 | | | | |
| Asp | Lys | Leu | Thr | Ile | Thr | Ser | Gln | Asn | Leu | Gln | Leu | Glu | Ser | Leu | Arg |
| 65 | | | | | 70 | | | | | 75 | | | | | 80 |
| Met | Lys | Leu | Pro | Lys | Ser | Ala | Lys | Pro | Val | Ser | Gln | Met | Arg | Met | Ala |
| | | | | 85 | | | | | 90 | | | | | 95 | |
| Thr | Pro | Leu | Leu | Met | Arg | Pro | Met | Ser | Met | Asp | Asn | Met | Leu | Leu | Gly |
| | | | | 100 | | | | | 105 | | | | | 110 | |
| Pro | Val | Lys | Asn | Val | Thr | Lys | Tyr | Gly | Asn | Met | Thr | Gln | Asp | His | Val |
| | | | | 115 | | | | | 120 | | | | | 125 | |
| Met | His | Leu | Leu | Thr | Arg | Ser | Gly | Pro | Leu | Glu | Tyr | Pro | Gln | Leu | Lys |
| | | 130 | | | | | 135 | | | | | 140 | | | |
| Gly | Thr | Phe | Pro | Glu | Asn | Leu | Lys | His | Leu | Lys | Asn | Ser | Met | Asp | Gly |
| 145 | | | | | 150 | | | | | 155 | | | | | 160 |
| Val | Asn | Trp | Lys | Ile | Phe | Glu | Ser | Trp | Met | Lys | Gln | Trp | Leu | Leu | Phe |
| | | | | 165 | | | | | 170 | | | | | 175 | |
| Glu | Met | Ser | Lys | Asn | Ser | Leu | Glu | Glu | Lys | Lys | Pro | Thr | Glu | Ala | Pro |
| | | | | 180 | | | | | 185 | | | | | 190 | |
| Pro | Lys | | | | | | | | | | | | | | |

<210> SEQ ID NO 6
<211> LENGTH: 601
<212> TYPE: DNA
<213> ORGANISM: Artificial Sequence
<220> FEATURE:
<223> OTHER INFORMATION: codon optimized nucleic acid

<400> SEQUENCE: 6

```
tataccatgg ctagcatgga cgaccaacgt gatctgatta gtaaccatga caactgccg      60
attctgggta accgcccgcg tgaaccggaa cgctcctccc gcggcgccct gtataccggt    120
gtgtccgttc tggtcgcact gctgctggcg ggtcaagcaa ccacggcata ttttctgtac    180
cagcaacagg gtcgtctgga taaactgacc attacgagtc aaaatctgca actggaatcc    240
ctgcgcatga aactgccgaa aagcgctaaa ccggtttctc agatgcgtat ggcaaccccg    300
ctgctgatgc gtccgatgag catggataac atgctgctgg gcccggtgaa aaacgttacc    360
aaatacggta acatgacgca agaccatgtc atgcacctgc tgacccgttc tggcccgctg    420
gaatacccgc agctgaaagg tacgtttccg gaaaacctga acatctgaa aaattcaatg    480
gacggcgtga actggaaaat cttcgaatcg tggatgaaac agtggctgct gtttgaaatg    540
tctaaaaact ccctggaaga aaaaaaaccg acggaagccc cgccgaaatg actcgagcac    600
c                                                                    601
```

<210> SEQ ID NO 7
<211> LENGTH: 194

```
<212> TYPE: PRT
<213> ORGANISM: Mus musculus

<400> SEQUENCE: 7

Met Ala Ser Met Asp Asp Gln Arg Asp Leu Ile Ser Asn His Glu Gln
1               5                   10                  15

Leu Pro Ile Leu Gly Asn Arg Pro Arg Glu Pro Glu Arg Cys Ser Arg
                20                  25                  30

Gly Ala Leu Tyr Thr Gly Val Ser Val Leu Val Ala Leu Leu Leu Ala
            35                  40                  45

Gly Gln Ala Thr Thr Ala Tyr Phe Leu Tyr Gln Gln Gln Gly Arg Leu
        50                  55                  60

Asp Lys Leu Thr Ile Thr Ser Gln Asn Leu Gln Leu Glu Ser Leu Arg
65                  70                  75                  80

Met Lys Leu Pro Lys Ser Ala Lys Pro Val Ser Gln Met Arg Met Ala
                85                  90                  95

Thr Pro Leu Leu Met Arg Pro Met Ser Met Asp Asn Met Leu Leu Gly
                100                 105                 110

Pro Val Lys Asn Val Thr Lys Tyr Gly Asn Met Thr Gln Asp His Val
            115                 120                 125

Met His Leu Leu Thr Arg Ser Gly Pro Leu Glu Tyr Pro Gln Leu Lys
    130                 135                 140

Gly Thr Phe Pro Glu Asn Leu Lys His Leu Lys Asn Ser Met Asp Gly
145                 150                 155                 160

Val Asn Trp Lys Ile Phe Glu Ser Trp Met Lys Gln Trp Leu Leu Phe
                165                 170                 175

Glu Met Ser Lys Asn Ser Leu Glu Glu Lys Lys Pro Thr Glu Ala Pro
                180                 185                 190

Pro Lys

<210> SEQ ID NO 8
<211> LENGTH: 601
<212> TYPE: DNA
<213> ORGANISM: Artificial Sequence
<220> FEATURE:
<223> OTHER INFORMATION: Codon optimized sequence

<400> SEQUENCE: 8
tataccatgg ctagcatgga cgaccaacgt gatctgatta gtaaccatga acaactgccg      60
attctgggta accgcccgcg tgaaccggaa cgctgctccc gcggcgccct gtataccggt     120
gtgtccgttc tggtcgcact gctgctggcg ggtcaagcaa ccacggcata ttttctgtac     180
cagcaacagg gtcgtctgga taaactgacc attacgagtc aaaatctgca actggaatcc     240
ctgcgcatga aactgccgaa aagcgctaaa ccggtttctc agatgcgtat ggcaaccccg     300
ctgctgatgc gtccgatgag catggataac atgctgctgg gcccggtgaa aaacgttacc     360
aaatacggta acatgacgca agaccatgtc atgcacctgc tgacccgttc tggcccgctg     420
gaatacccgc agctgaaagg tacgtttccg gaaaacctga acatctgaa aaattcaatg     480 gacggcgtga actggaaaat cttcgaatcg tggatgaaac agtggctgct gtttgaaatg     540
tctaaaaact ccctggaaga aaaaaaaccg acggaagccc cgccgaaatg actcgagcac     600
c                                                                    601
```

RECOMBINANT CD74 POLYPEPTIDES

CROSS REFERENCE TO RELATED APPLICATION

This claims the benefit of U.S. Provisional Application No. 62/353,497, filed Jun. 22, 2016, which is incorporated herein by reference in its entirety.

ACKNOWLEDGEMENT OF GOVERNMENT SUPPORT

This invention was made with government support under NS047661 awarded by the National Institutes of Health. The government has certain rights in the invention.

FIELD

Generally, this disclosure relates to the production of recombinant proteins, in particular the recombinant production of soluble eukaryotic proteins in bacterial cells.

BACKGROUND

CD74 is a chaperone that assists with the folding and trafficking of Class II MHC. It has a structure characterized by an un-folded domain near the N-terminus, with a more organized domain conformation at the C-terminus. This C-terminal domain trimerizes with other CD74 molecules. CD74 is the receptor for macrophage migration inhibitory factor (MIF) and D-dopachrome tautomerase (D-DT).

SUMMARY

A soluble recombinant CD74 (invariant chain) polypeptide that is capable of binding CD74 ligands such as MIF, D-DT, RTL1000, and/or DRα1 is unavailable commercially at the time of filing. Clearly such active forms are needed to facilitate further research.

Disclosed herein are active soluble forms of CD74 (invariant chain) that bind to natural and recombinant CD74 ligands such as MIF, D-DT, RTL-1000, and/or DRα1 (such as DRα1-MOG-35-55). Said recombinant polypeptides include a polypeptide of SEQ ID NO: 1, SEQ ID NO: 3, or SEQ ID NO: 5 or any polypeptide comprising one or more conservative amino acid substitution mutations relative to SEQ ID NO: 1, SEQ ID NO: 3, or SEQ ID NO: 5, provided that the conservative amino acid substitution mutation is not a C27S mutation in SEQ ID NO: 3 or SEQ ID NO: 5 and provided that the polypeptide comprising the at least one or more conservative amino acid substitution mutations binds a CD74 ligand with at least 50% the affinity of SEQ ID NO: 1, SEQ ID NO: 3, or SEQ ID NO: 5. In some examples, the CD74 ligand comprises MIF, D-DT, RTL1000, or DRα1 (such as DRα1-MOG-35-55). In still further examples, the polypeptide includes no more than 20 amino acid substitution mutations relative to SEQ ID NO: 1, SEQ ID NO: 3 or SEQ ID NO: 5. In some examples, the recombinant polypeptide further comprises a label such as a fluorescent dye, protein tag, fluorescent protein, or biotin.

Disclosed herein are polynucleotides that encode the disclosed polypeptides. The polynucleotides in some examples are codon optimized for expression in any system including E. coli. In some examples, the polynucleotide comprises SEQ ID NO: 2, SEQ ID NO: 4, SEQ ID NO: 6, SEQ ID NO: 8, or a polynucleotide comprising one or more silent mutations or one or more mutations that result in a conservative amino acid substitution in the encoded polypeptide, provided that the polynucleotide comprising the silent mutation or the mutation that results in a conservative amino acid substitution in the encoded polypeptide is expressed in E. coli at least 50% of the level of that of SEQ ID NO: 2, SEQ ID NO: 4, SEQ ID NO: 6, or SEQ ID NO: 8.

Disclosed herein are expression vectors comprising one or more of the disclosed polynucleotides and a promoter operably linked to the polynucleotide. The promoter can be any promoter including a constitutively active, conditional, or inducible promoter.

Disclosed herein are bacterial cells (such as E. coli cells) comprising the disclosed expression vectors.

Disclosed herein are methods of producing the disclosed polypeptides. The methods involve inoculating a media with a disclosed bacterial cell comprising the expression vector (for example, a disclosed E. coli cell), inducing expression of the disclosed polypeptide, and purifying the disclosed polypeptide from inclusion bodies.

BRIEF DESCRIPTION OF THE SEVERAL VIEWS OF THE DRAWINGS

FIG. 2 is set of two graphs that collectively show the binding of hMIF to the rhCD74 of SEQ ID NO: 1. Fifty μl of hMIF was coated onto ELISA plates at a concentration of 0.5 μg/ml and 1 μg/ml overnight at 4° C. Then, excess hMIF was washed and wells were blocked with 5% BSA in PBS pH 7.4 for 2 hours at 25° C. After blocking, wells were washed again and serial dilutions of rhCD74 starting at 2.5 μg/ml or 5.0 μg/ml were captured for 1 hour at 25° C. Unbound material was washed out as described above and rhCD74 was detected with PIN.1/anti-mouse-HRP (2.5 μg/2 μg in 5 ml of blocking buffer) for 1.5 hours at 25° C. Color development was started by adding HRP substrate while the reaction continued for 10 min. Enzyme activity was stopped by adding 50 μl of stop solution (1N HCl in water). Color intensity was read at 450 nm in an ELISA plate reader. Rows H1 through H12 were controls: wells contain no MIF but the highest concentration of rhCD74 (2.5 μg/ml or 5.0 μg/ml) were applied to measure unspecific binding. The graph on the left represents the saturation of the binding and the graph on the right shows just the relevant points.

FIG. 3 is a bar graph showing the binding of RTL1000 to the rhCD74 of SEQ ID NO: 1. RTL1000 (1:2 dilution) was evaluated for its binding ability to rhCD74 in ELISA. rhCD74 at 1 μg/ml was coated onto wells overnight at 4° C. and excess protein was removed by washing the wells 4 times with PBS/0.0125% T20 at 25° C. Blocking was performed with 5% BSA/PBS pH 7.4 for 2 hours at 25° C. and then wells were washed again as above. Capture of different concentrations of RTL1000 was carried out at 25° C. for 2 hours and after washing, unbound protein wells were washed again. Bound RTL1000 was detected by probing the wells with mAb TU39 (1.25 μg/5 ml)/anti-mouse IgG-HRP (1 μg/5 ml) together for 1.5 hours at 25° C. Color was developed for 5 minutes and then absorbance was read in an ELISA plate reader at 450 nm. Wells H1-H12 were coated with just blocking solution but treated with RTL1000 at the maximum concentration and served as a control to determine background.

FIG. 6 is a graph showing binding of rmCD74 C27S (SEQ ID NO: 5) and rhCD74 C27S (SEQ ID NO: 3) to D-DT. 50 μl of D-DT at 1 μg/ml in PBS were coated for 2 hours at 25° C. and then the wells were blocked with 5% BSA in PBS and 0.05% Tween 20 (5% BSA/PBS/T20). Serial dilutions of recombinant CD74, either the murine or the human version, were applied to the wells let to bind for another 2 hours at the same temperature. Wells were washed and CD74 bound to DDT was detected with the monoclonal antibody MB-741 (which recognizes both version of the CD74) and anti-mouse antibody conjugated to HRP. Color development was started adding the HRP substrate to the wells and then absorbance was determined by reading the plate at 450 nm. Graph was generated using Prism software.

SEQUENCE LISTING

Figure 1:
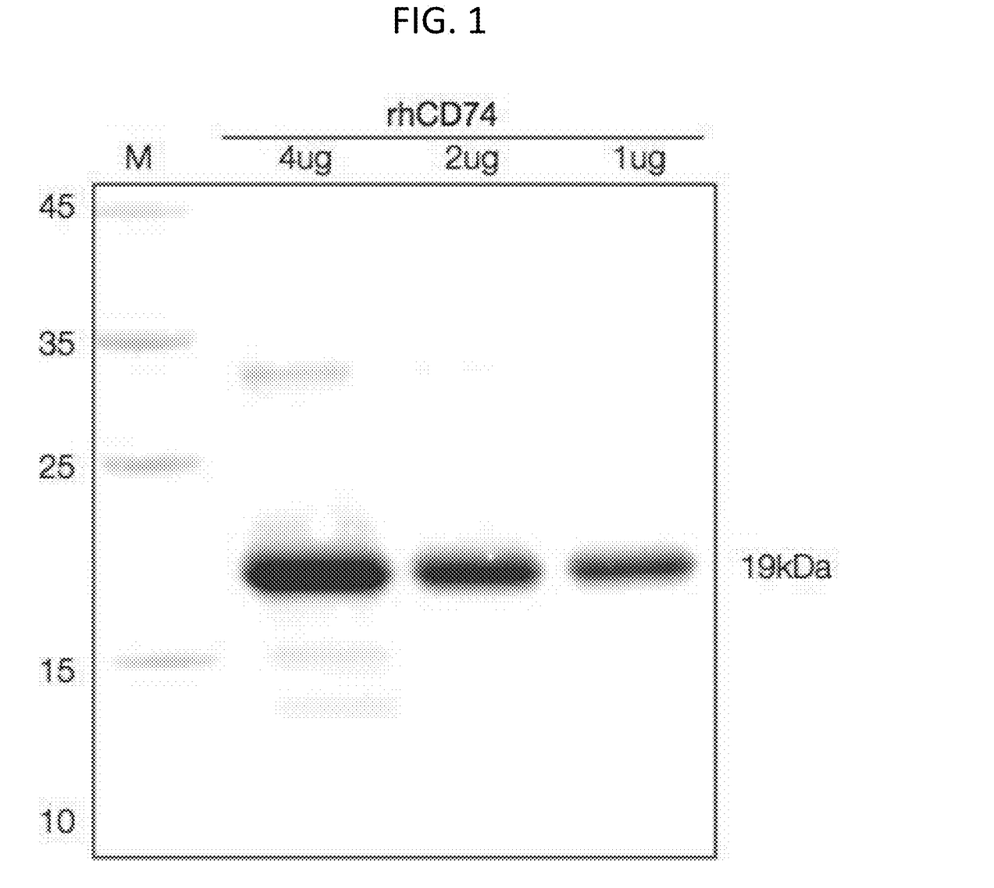
FIG. 1 is a digital image of the recombinant mouse-human chimeric CD74 (rhCD74) of SEQ ID NO: 1 in a reducing Tris-HCl 10-20% gradient polyacrylamide gel. Samples containing 4, 2 and 1 μg of protein were loaded onto the gel, stained with Coomassie Blue dye and scanned. The protein shows a 19 kDa migration index as evaluated by using a protein standard with known molecular sizes.
Figure 2:
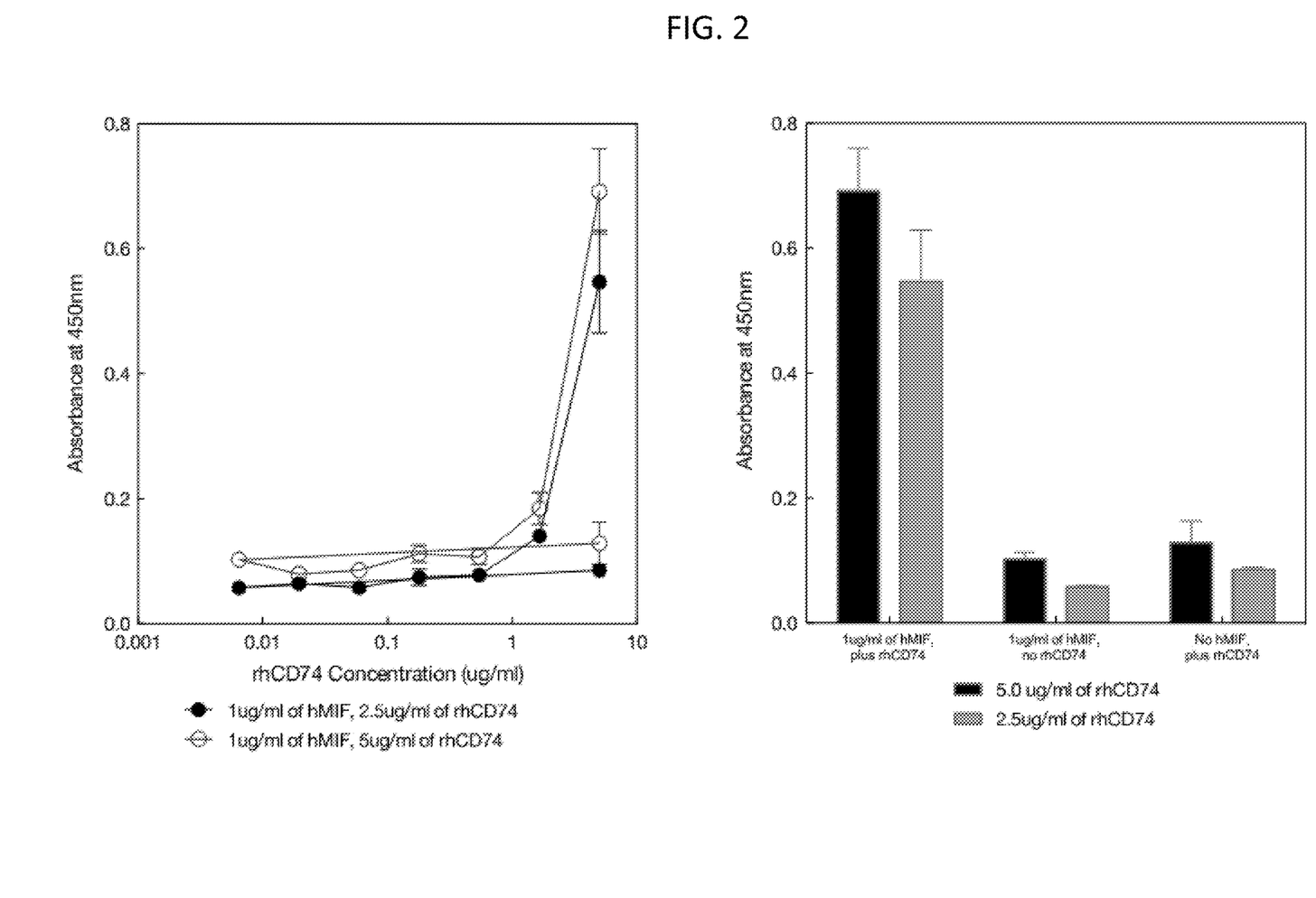
Figure 3:
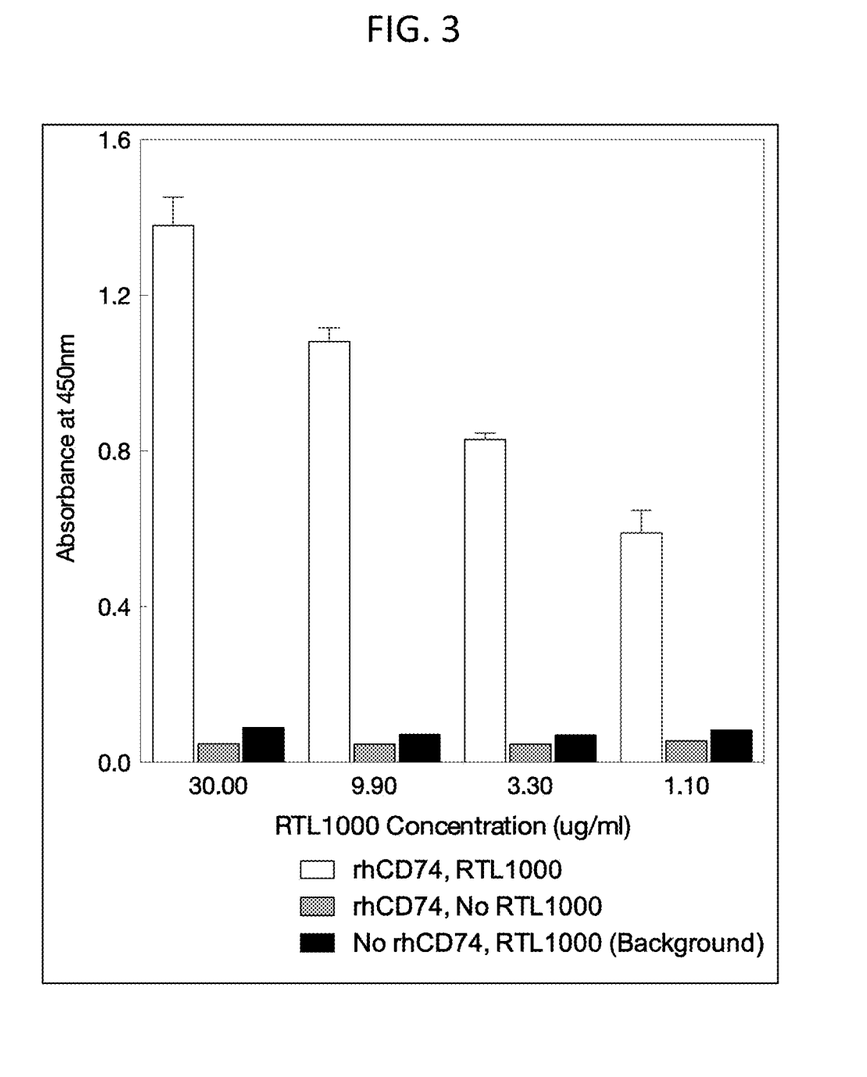
Figure 4:
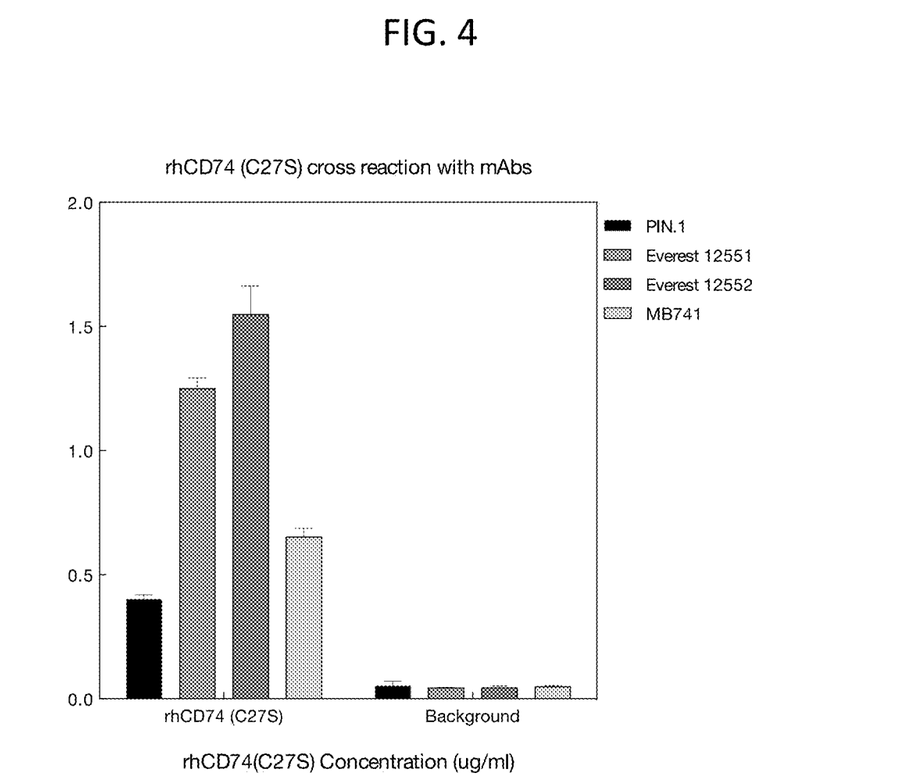
FIG. 4 is a bar graph showing that the rhCD74 with C27S mutation of SEQ ID NO: 3 is recognized by several monoclonal anti-human CD74 antibodies. Fifty μl of rhCD74 was coated onto an ELISA plate at a concentration of 0.5 μg/ml for 1.5 hours at 25° C. Then, non-coated protein was washed out 4 times with PBS/0.0125% T20 and then blocked for 2 hours at 25° C. with 5% BSA/PBS/T20. Antibodies/HRP-conjugated anti-antibodies were added at 1 μg/ml in blocking solution for 1.5 hours at 25° C. and the unbound antibodies were washed out as above. Color development was allowed after adding the HRP substrate TMB. As a negative control and to determine the background, one row of wells was not coated with rhCD74 but was treated with antibody/anti-antibody mixture.
Figure 5A:
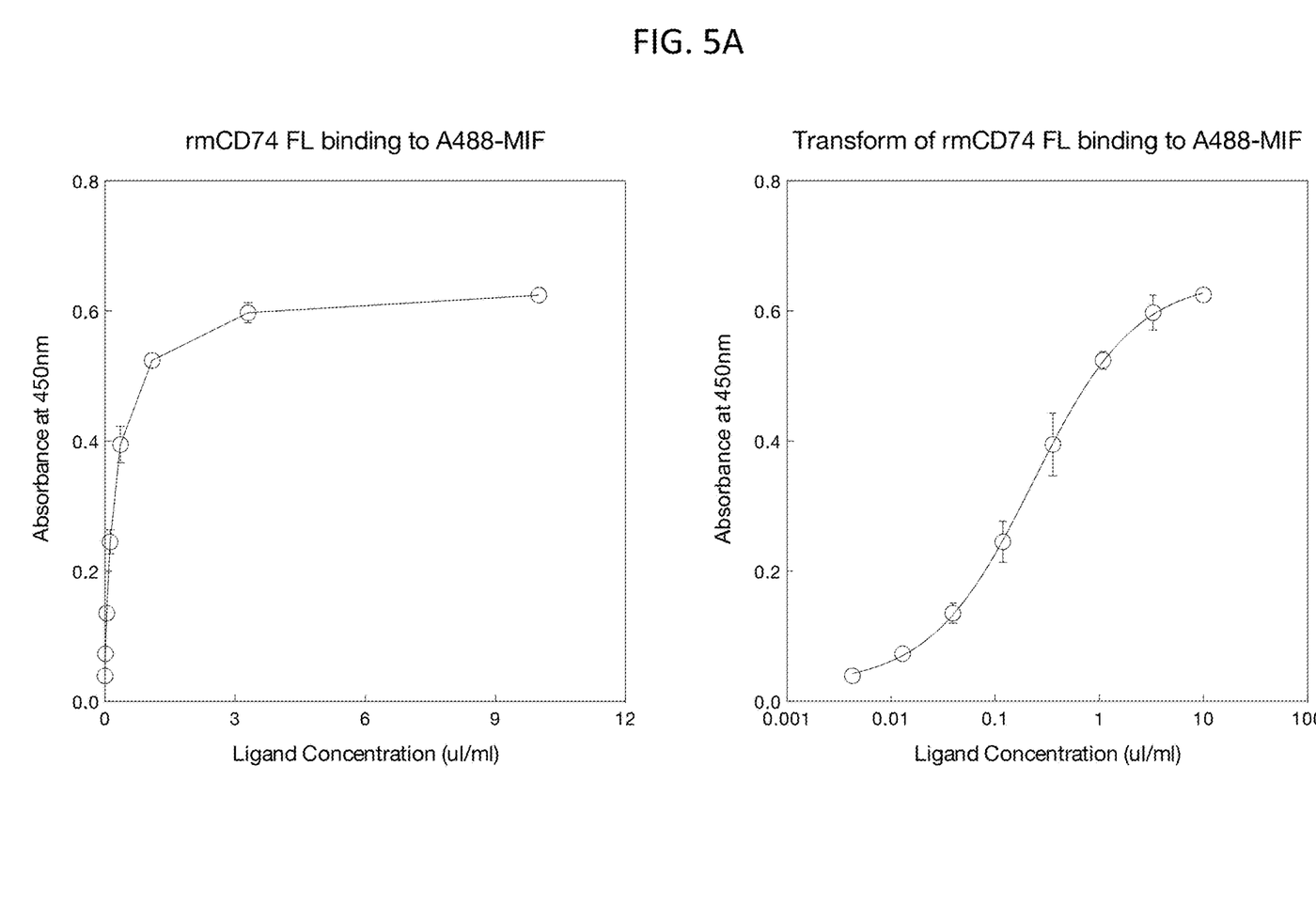
FIG. 5A is a set of plots showing the results where recombinant human MIF was coated onto wells of an ELISA plate and recombinant mouse CD74 (rmCD74; SEQ ID NO: 7) was added. Binding was allowed to proceed for 1 hour at 25° C. Wells were probed with the mouse CD74 monoclonal antibody In1. Non-specific binding was tested by adding rmCD74 to non-coated, blocked wells. Left panel shows the x-axis on a linear scale. Right panel shows the x-axis on a logarithmic scale.
Figure 5B:
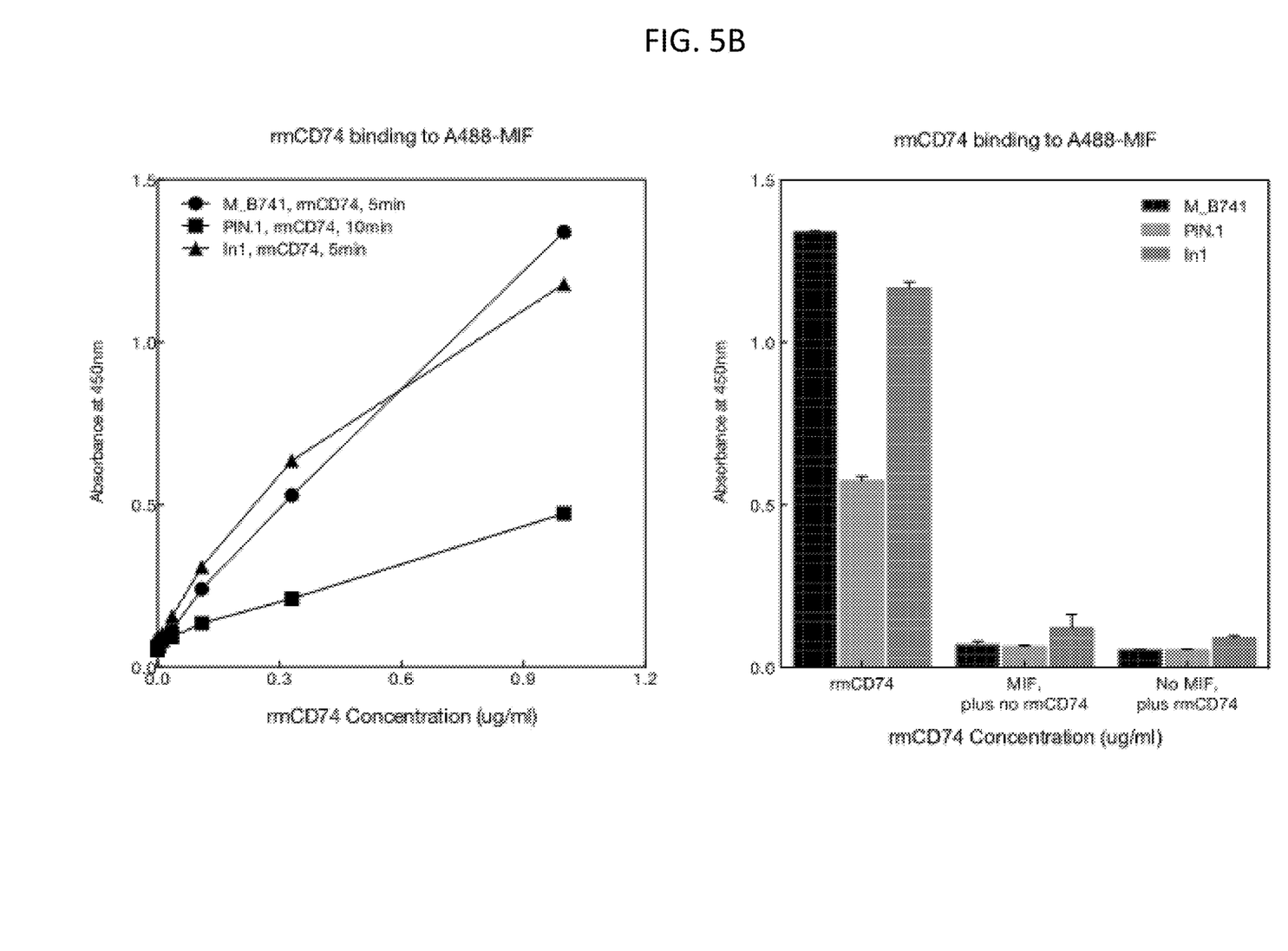
FIG. 5B is a plot and a bar graph showing binding of rmCD74 (SEQ ID NO: 7) to human MIF as described above except that three different anti-mouse CD74 monoclonal antibodies (MB-741, PIN1, and In1 are compared). The bar graph (right panel) recapitulates the results shown for the 1 μg/ml concentration shown in the plot (left panel).
Figure 6:
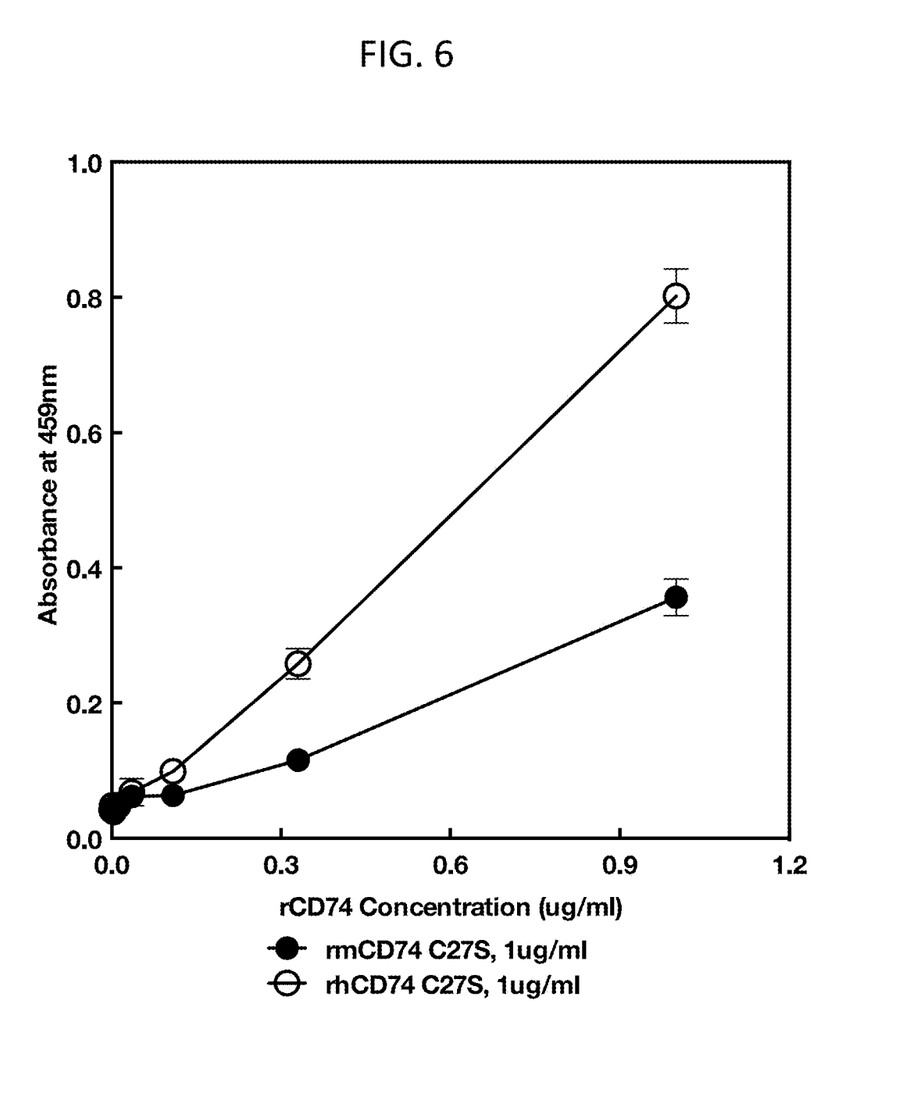

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Jun. 21, 2017, and is 11,062 bytes, which is incorporated by reference herein.

SEQ ID NO: 1 is a polypeptide sequence of a mouse-human chimera CD74 with amino acids 1-54 from the mouse and amino acids 55-190 from the human.

SEQ ID NO: 2 is a codon optimized polynucleotide sequence for the expression of SEQ ID NO: 1 in *E. coli*.

SEQ ID NO: 3 is a polypeptide sequence of the mouse-human chimera CD74 of SEQ ID NO: 1, further comprising an engineered C27S mutation.

SEQ ID NO: 4 is a codon optimized polynucleotide sequence for the expression of SEQ ID NO: 3 in *E. coli*.

SEQ ID NO: 5 is a polypeptide sequence of murine CD74 comprising an engineered C27S mutation.

SEQ ID NO: 6 is a codon optimized polynucleotide sequence for the expression of SEQ ID NO: 5 in *E. coli*.

SEQ ID NO: 7 is a polypeptide sequence of wild type murine CD74.

SEQ ID NO: 8 is a codon optimized polynucleotide sequence for the expression of SEQ ID NO: 7 in *E. coli*.

DETAILED DESCRIPTION

I. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In addition, the materials, methods, and examples are illustrative only and not intended to be limiting. In order to facilitate review of the various embodiments of the disclosure, the following explanations of specific terms are provided:

Antibody: A polypeptide including at least a light chain or heavy chain immunoglobulin variable region which specifically recognizes and binds an epitope of an antigen or a fragment thereof. Antibodies are composed of a heavy and a light chain, each of which has a variable region, termed the variable heavy (VH) region and the variable light (VL) region. Together, the VH region and the VL region are responsible for binding the antigen recognized by the antibody. The VH and VL regions can be further segmented into complementarity determining regions (CDRs) and framework regions. The CDRs (also termed hypervariable regions) are the regions within the VH and VL responsible for antibody binding.

The term "antibody" encompasses intact immunoglobulins, as well the variants and portions thereof, such as Fab fragments, Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker. In dsFvs the chains have been mutated to introduce a disulfide bond to stabilize the association of the chains. The term also includes genetically engineered forms such as chimeric antibodies and heteroconjugate antibodies (such as, bispecific antibodies). See also, Pierce Catalog and Handbook, 1994-1995 (Pierce Chemical Co., Rockford, Ill.); Kuby, J., *Immunology*, 3rd Ed., W.H. Freeman & Co., New York, 1997.

The term also includes monoclonal antibodies (all antibody molecules have the same VH and VL sequences and therefore the same binding specificity) and polyclonal antisera (the antibodies vary in VH and VL sequence but all bind a particular antigen such as a tissue antigen).

An antibody can be used in combination with the disclosed compositions and methods in labeling multiple proteins of interest, including proteins that are expressed on the cell surface.

CD74: Also known as CD74 molecule, major histocompatibility complex gamma chain, or class II invariant chain. CD74 is a chaperone regulating antigen presentation during immune response. It is also a cell surface receptor for macrophage migration inhibitory factor (MIF) and its homolog, D-dopachrome tautomerase (D-DT).

Nucleic acid and protein sequences for CD74 are publicly available. For example, GenBank Accession Nos. NM_001025158, NM_004355, and NM_001025159 disclose exemplary human CD74 nucleic acid sequences, and GenBank Accession Nos. NP 001020329, NP_004346, and NP_001020330 disclose exemplary human CD74 amino acid sequences. Similarly, GenBank Accession Nos. NM_001042605 and NM_010545 disclose exemplary mouse CD74 nucleic acid sequences, and GenBank Accession Nos. NP_001036070 and NP_034675 disclose exemplary mouse CD74 amino acid sequences. Each of these sequences is incorporated herein by reference as present in GenBank on Oct. 16, 2015.

Conservative amino acid substitution: A substitution of an amino acid residue for another amino acid residue having similar biochemical properties. "Conservative" amino acid substitutions are those substitutions that do not substantially affect or decrease an activity of a polypeptide such as a DNA ligase binding domain or a fluorescent protein. A polypeptide can include one or more conservative substitutions up to and including 1-10 total conservative substitutions, 1% conservative substitutions, 5% conservative substitutions, 10% conservative substitutions, 15% conservative substitutions, 20% conservative substitutions, 25% conservative substitutions, 30% or more conservative substitutions, or any intervening value.

While examples of polypeptide sequences are provided in the amino acid sequences attached to this application, not all variants of polypeptide sequences with all possible combinations of conservative amino acid substitutions encompassed by the disclosure are provided in the sequence listing. Specific, non-limiting examples of a conservative substitution include the following examples:

| Original Amino | Conservative |
| --- | --- |
| Ala | Ser |
| Arg | Lys |
| Asn | Gln, His |
| Asp | Glu |
| Gln | Asn |
| Cys | Ser |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

This table can be used in combination with the sequence listing to provide explicit examples of polypeptide sequences encompassed by the disclosure.

Isolated: An "isolated" biological component (such as a nucleic acid, peptide or protein) has been substantially separated, produced apart from, or purified away from other biological components in the cell of the organism in which the component occurs, e.g., other chromosomal and extra-chromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell, as well as chemically synthesized nucleic acids.

Label: A label can be any substance capable of aiding a machine, detector, sensor, device, column, or enhanced or unenhanced human eye from differentiating a labeled composition from an unlabeled composition. Labels may be used for any of a number of purposes and one skilled in the art will understand how to match the proper label with the proper purpose. Examples of uses of labels include purification of biomolecules, identification of biomolecules, detection of the presence of biomolecules, detection of protein folding, and localization of biomolecules within a cell, tissue, or organism. Examples of labels include but are not limited to: radioactive isotopes (such as carbon-14 ($^{14}C$) or chelates thereof; dyes (fluorescent or non-fluorescent), stains, enzymes, nonradioactive metals, magnets, protein tags, small molecules, haptens, either half of a receptor/ligand pair, any antibody epitope, any specific example of any of these; any combination between any of these, or any label now known or yet to be disclosed. A label may be covalently attached to a biomolecule or bound through hydrogen bonding, Van Der Waals or other forces. A label may be covalently or otherwise bound to the N-terminus, the C-terminus or any amino acid of a polypeptide.

One particular example of a label is a small molecule fluorescent dye. Such a label can be conjugated to a polypeptide. One of skill in the art would be able to identify and select any appropriate fluorescent dye or combination of fluorescent dyes for use in the disclosed methods.

Another particular example of a label is an enzyme. In specific examples, the enzyme is conjugated to a polypeptide. After an enzyme labeled polypeptide is bound to a ligand, a substrate for the enzyme is then added to the antibody. In some examples, the activity of the enzyme in the presence of the specific substrate results in a color change that indicates the presence of the label. Such a reaction can be termed a chromogenic reaction. Non-limiting examples of enzyme labels include horseradish peroxidase, alkaline phosphatase, glucose oxidase, and β-galactosidase.

Another particular example of a label is a protein tag. A protein tag comprises a sequence of one or more amino acids that may be used as a label as discussed above, particularly for use in protein purification. In some examples, the protein tag is covalently bound to the polypeptide. It may be covalently bound to the N-terminal amino acid of a polypeptide, the C-terminal amino acid of a polypeptide or any other amino acid of the polypeptide. Often, the protein tag is encoded by a polynucleotide sequence that is immediately 5' of a nucleic acid sequence coding for the polypeptide such that the protein tag is in the same reading frame as the nucleic acid sequence encoding the polypeptide. Protein tags may be used for all of the same purposes as labels listed above and are well known in the art. Examples of protein tags include chitin binding protein (CBP), HA, maltose binding protein (MBP), glutathione-S-transferase (GST), poly-histidine (His), thioredoxin (TRX), FLAG®, V5, c-Myc, HA-tag, and so forth.

A His-tag facilitates purification and binding to metal matrices, including nickel matrices, for example nickel matrices bound to solid substrates such as agarose plates or beads, glass plates or beads, or polystyrene or other plastic plates or beads.

Another particular example of a label is biotin. Biotin is a naturally occurring compound that is an enzyme cofactor with a number of effects in the body. Biotin is also used as a protein label due to its small size, which generally does not affect protein structure or activity. In addition, biotin binds to streptavidin or avidin with very high affinity and is therefore very easily captured by streptavidin/avidin conjugated columns, beads, plates, etc. A number of methods well known in the art have adapted the biotin/(strept)avidin interaction for purification of biotinylated proteins. Alternatively, the label may comprise streptavidin.

Another particular example of a label is a fluorescent protein such as green fluorescent protein (GFP) modified GFPs and GFP derivatives and other fluorescent proteins, such as EGFP, EBFP, YFP, BFP, CFP, ECFP Clover, mKate, and so forth.

Mutation: A mutation can be any difference in the sequence of a biomolecule relative to a reference or consensus sequence of that biomolecule. A mutation can be observed in a nucleic acid sequence or a protein sequence. Such a reference or consensus sequence may be referred to as "wild type". A mutation can be purposefully engineered into a polypeptide through recombinant DNA technology.

Operably Linked: A first nucleic acid sequence is operably linked with a second nucleic acid sequence when the first nucleic acid sequence is placed in such a way that it has an effect upon the second nucleic acid sequence. For instance, a promoter is operably linked to a coding sequence if the promoter affects the transcription or expression of the coding sequence. Operably linked DNA sequences may be contiguous, or they may operate at a distance.

Polynucleotide: a polymer of ribonucleic acid (RNA) or deoxyribonucleic acid (DNA). A nucleic acid is made up of four bases; adenine, cytosine, guanine, and thymine/uracil (uracil is used in RNA). A coding sequence from a nucleic acid is indicative of the sequence of the protein encoded by the nucleic acid. Polynucleotide sequences are generally written with the 5' end on the left and the 3' end on the right.

Polypeptide: Any chain of amino acids, regardless of length or post-translational modification (such as glycosylation, methylation, ubiquitination, phosphorylation, or the like). Herein as well as in the art, the term "polypeptide" is used interchangeably with peptide or protein, and is used to refer to a polymer of amino acid residues. The term "residue" can be used to refer to an amino acid or amino acid mimetic incorporated in a polypeptide by an amide bond or amide bond mimetic. Polypeptide sequences are generally written with the N-terminal amino acid on the left and the C-terminal amino acid to the right of the sequence.

Promoter: A promoter can be any of a number of nucleic acid control sequences that directs transcription of a nucleic acid. Expression by a promoter may be further modulated by enhancer or repressor elements. Numerous examples of promoters are available and well known to those of skill in the art. A nucleic acid comprising a promoter operably linked to a nucleic acid sequence that codes for a particular polypeptide can be termed an expression vector. An expression vector comprising a constitutively active promoter expresses the protein at effectively all times in the cell. A conditionally active promoter directs expression only under certain conditions. For example, a conditionally active promoter might direct expression only in the presence or absence of a particular compound such as a small molecule, amino acid, nutrient, or other compound while a constitutively active promoter directs expression independently of such conditions. A conditionally active promoter can also be termed an inducible promoter. An example of a compound that induces expression of particular conditionally active/inducible promoters is IPTG.

Purified: The term purified does not require absolute purity; rather, it is intended as a relative term. Thus, for example, a purified peptide preparation is one in which the peptide or protein is more enriched than the peptide or protein is in its environment, for example within a cell or in a preparation. Preferably, a preparation is purified such that the protein or peptide represents at least 50% of the total peptide or protein content of the preparation. In some embodiments, a purified preparation contains at least 60%, at least 70%, at least 80%, at least 85%, at least 90%, at least 95% or more of the protein or peptide.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques. A recombinant polypeptide can also refer to a polypeptide that has been made using recombinant nucleic acids, including recombinant nucleic acids transferred to a host organism that is not the natural source of the polypeptide.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage identity or similarity (which takes into account conservative amino acid substitutions); the higher the percentage, the more similar the sequences are. Polypeptides or protein domains thereof that have a significant amount of sequence identity and also function the same or similarly to one another (for example, proteins that serve the same functions in different species or mutant forms of a protein that do not change the function of the protein or the magnitude thereof) can be called "homologs."

Methods of alignment of sequences for comparison are well known in the art. Various programs and alignment algorithms are described in: Smith & Waterman, *Adv Appl Math* 2, 482 (1981); Needleman & Wunsch, *J Mol Biol* 48, 443 (1970); Pearson & Lipman, *Proc Natl Acad Sci USA* 85, 2444 (1988); Higgins & Sharp, *Gene* 73, 237-244 (1988); Higgins & Sharp, *CABIOS* 5, 151-153 (1989); Corpet et al, *Nuc Acids Res* 16, 10881-10890 (1988); Huang et al, *Computer App Biosci* 8, 155-165 (1992); and Pearson et al, *Meth Mol Bio* 24, 307-331 (1994). In addition, Altschul et al, *J Mol Biol* 215, 403-410 (1990), presents a detailed consideration of sequence alignment methods and homology calculations.

The NCBI Basic Local Alignment Search Tool (BLAST) (Altschul et al, (1990) supra) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr database, swissprot database, and patented sequences database. Queries searched with the blastn program are filtered with DUST (Hancock & Armstrong, *Comput Appl Biosci* 10, 67-70 (1994.) Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein.

When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 50%, 60%, 70%, 80%, 90%, 95%, 98%, or 99% sequence identity to a nucleic acid that encodes a protein.

Specific binding: An association between two substances or molecules such as the association of a polypeptide with its ligand (for example, CD74 with MIF, D-DT, or another ligand such as an RTL or DRα1 (such as DRα1-MOG-35-55)). As disclosed here, the polypeptide has specificity for the ligand to the exclusion of other, non-similar ligands. Binding can be detected by any procedure known to one skilled in the art, such as by physical or functional properties. Binding can also be detected by visualization of a label conjugated to the polypeptide.

II. Polypeptides and Vectors

Disclosed herein are polypeptide compositions comprising SEQ ID NO: 1. Amino acids 1-54 of SEQ ID NO: 1 are derived from the intracellular and trans-membrane domains of mouse CD74 and amino acids 55-190 are derived from the extracellular domain of human CD74 comprising the CLIP region and the trimerization domain. Also disclosed are polypeptide sequences that are mutated relative to SEQ ID NO: 1 by one or more amino acids provided that the mutant polypeptide has the same or similar activity to SEQ ID NO: 2 in one or more characteristics (such as binding of a ligand such as MIF, D-DT, a recombinant T cell ligand, or a DRα1 polypeptide (such as DRα1-MOG-35-55)).

In some examples, the mutant polypeptides comprise at least 1, at least 2, at least 3, at least 4, at least 5, at least 7, at least 10, at least 15, at least 20, or 25 or more amino acid substitution mutations. In still further examples, the amino acid substitution mutations are conservative amino acid substitution mutations.

Examples of methods that measure CD74 activity are available to one of skill in the art and are provided in the examples below. The mutant polypeptide can have a similar activity of at least 50%, at least 55%, at least 60%, at least 65%, at least 70%, at least 75%, at least 80%, at least 85% at least 90%, at least 95%, at least 98%, at least 99%, or 100% of the level, or more than 100% of the activity of the polypeptide of SEQ ID NO: 2.

The polypeptide compositions also comprise SEQ ID NO: 3. Also disclosed are polypeptide sequences that are mutated relative to SEQ ID NO: 3 by one or more amino acids provided that the mutant polypeptide has the same or similar activity to SEQ ID NO: 2 in some characteristic (such as binding of a ligand such as MIF, D-DT, a recombinant T cell ligand, or a DRα1 polypeptide (such as DRα1-MOG-35-55)).

In some examples, the mutant polypeptides comprise at least 1, at least 2, at least 3, at least 4, at least 5, at least 7, at least 10, at least 15, at least 20, or 25 or more amino acid substitution mutations relative to SEQ ID NO: 4. In still further examples, the amino acid substitution mutations are conservative amino acid substitution mutations.

Examples of methods that measure CD74 activity are available to one of skill in the art and are provided in the examples below. The mutant polypeptide can have at least 50%, at least 55%, at least 60%, at least 65%, at least 70%, at least 75%, at least 80%, at least 85% at least 90%, at least 95%, at least 98%, at least 99%, or 100% of the level or more than 100% of the activity of the polypeptide of SEQ ID NO: 4.

SEQ ID NOs: 3 and 5 are polypeptides that include a cysteine at position 27 mutated to serine. Without the mutation, these polypeptides can dimerize during purification and storage, resulting in dimerized CD74 trimers. This dimerization could result in inaccurate binding data for CD74 in vitro.

The polypeptide compositions can comprise conservative amino acid substitutions. Examples of conservative amino acid substitutions include Ala→Ser; Arg→Lys; Asn→Gln, His; Asp→Glu; Cys→Ser; Gln→Asn; Glu→Asp; His→Asn, Gln; Ile→Leu, Val; Leu→Ile, Val; Lys→Arg, Gln, Glu; Met→Leu, Ile; Phe→Met, Leu, Tyr; Ser→Thr; Thr→Ser; Trp→Tyr; Tyr→Trp, Phe; Val→Ile, Leu. Other potential amino acid substitutions include substitution of one or more amino acids derived from the mouse extracellular domain with the corresponding amino acid from the human extracellular domain.

In additional embodiments, the disclosed polypeptides include a tag or label (such as an N-terminal or C-terminal label), for example for use in protein purification. One of skill in the art can select appropriate tags, such as a His-tag, a GST tag, or an antibody recognition sequence (such as a Myc-tag or HA-tag). The polypeptide can also be produced as a fusion protein, either to facilitate expression and/or purification or to facilitate delivery to a subject. In other examples, the polypeptide may include a detectable label, such as a radioisotope, fluorophore, or hapten.

Disclosed herein are polynucleotide compositions, expression vectors, polypeptides, and recombinant bacteria (such as *E. coli*) that express polypeptides of a human-mouse chimera CD74. The polynucleotide compositions include a polynucleotide sequence that is codon optimized for expression in *E. coli*, yeast, or mammalian cells such as SEQ ID NO: 2, SEQ ID NO: 4, SEQ ID NO: 6, and SEQ ID NO: 8 which are codon optimized for expression in *E. coli*. Also disclosed are polynucleotide sequences that are mutated relative to SEQ ID NO: 2 by one or more nucleotides provided that the expressed polypeptide from the mutant polynucleotide is expressed at the same or a similar yield. The mutant can be expressed at least 50%, at least 55%, at least 60%, at least 65%, at least 70%, at least 75%, at least 80%, at least 85% at least 90%, at least 95%, at least 98%, at least 99%, or 100% of the level or more than 100% of the polynucleotide of SEQ ID NO: 2.

The polynucleotides can be cloned into any applicable plasmid vector such as an expression vector. The expression vector comprises a promoter that drives transcription of mRNA from the coding sequence for the polypeptide and translation of the mRNA into the protein. The promoter can be any promoter such as a constitutively active, inducible, or conditional promoter or a promoter specific for expression in the cell type or bacterium in which the polypeptides are expressed. The promoter is operably linked to the oligonucleotide. The expression vector can also comprise transcriptional enhancers, silencers, repressors, or any other transcriptional element that can be useful in expression.

Also disclosed herein are bacterial cells (such as *E. coli, Bacillus subtilis,* or *Brevibacillus* bacterial cells) comprising an expression vector that encodes a polypeptide of SEQ ID NO: 1, SEQ ID NO: 3, SEQ ID NO: 5, SEQ ID NO: 7, or any mutant that has the same or similar activity thereto. The expression vector comprises a polynucleotide that encodes the polypeptide (including the codon optimized polynucleotide of SEQ ID NO: 2 or SEQ ID NO: 4, SEQ ID NO: 6, SEQ ID NO: 8, or any mutant that is expressed at the same or similar level), where the polynucleotide is operably linked to a promoter that drives expression of the polynucleotide into the polypeptide in the bacterial cell.

Also disclosed are eukaryotic cells, such as yeast (e.g., *Saccharomyces, Pichia,* or *Kluyveromyces*), insect (e.g., Sf9), or mammalian (e.g., CHO or HEK 293) cells, comprising an expression vector that encodes a polypeptide of SEQ ID NO: 1, SEQ ID NO: 3, SEQ ID NO: 5, SEQ ID NO: 7, or any mutant that has the same or similar activity thereto. The expression vector comprises a polynucleotide that encodes the polypeptide, where the polynucleotide is operably linked to a promoter that drives expression of the polynucleotide into the polypeptide in the eukaryotic cell.

III. Expression, Induction, and Purification

Methods of expression and purification of the polypeptides from inclusion bodies are also disclosed herein. The methods include inoculating a culture medium with a cell comprising an expression vector that encodes one of the disclosed CD74 polypeptides. One of ordinary skill in the art can select an appropriate culture medium based on the cell in which the expression vector is included.

In some examples, the methods include inoculating a culture medium (such as LB or other bacterial media) with a bacterium comprising an expression vector that expresses one of the disclosed CD74 polypeptides. One example of the expression vector is pET21d(+). A polynucleotide sequence that encodes one of the disclosed CD74 polypeptides can be cloned into the polylinker of such a vector. The bacterium can be any appropriate bacterial strain such as an *E. coli* strain, including BL21(DH3). The culture provides a mechanism for selective growth of bacteria comprising the expression vector within the culture. In some examples, this mechanism involves the expression vector expressing a drug resistance gene and further involves the addition of the drug (to which the drug resistance gene confers resistance) to the media. Such drug/resistance gene combinations for selection for plasmid are well known in the art. Drugs used in such selection include ampicillin, carbenicillin, kanamycin, zeocin, blasticidin, spectinomycin, gentamycin, tetracycline, chloramphenicol, and hygromycin.

Expression of the disclosed CD74 polypeptides can be induced, for example, by treating with a compound such as IPTG at a proper time (such as when the OD600 of the culture=0.7). The culture can be allowed to grow for a period of time after induction, such as at least four hours. The culture can then be spun in a centrifuge, the pellet sonicated and inclusion bodies purified. CD74 protein can be solubilized in an appropriate buffer (such as PBS pH 7.4), which can further contain a low concentration of SDS (such as 0.05%). The solubilization can be performed at room temperature for a period of at least one hour. The SDS can be removed from the solution through dialysis in, for example, a PBS buffer. Purity of the protein can be analyzed using SDS-PAGE electrophoresis including, for example, 10%-20% denaturing and reducing PAGE.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

The invention claimed is:

1. A recombinant polypeptide comprising: the amino acid sequence of SEQ ID NO: 1 or SEQ ID NO: 3.

2. The polypeptide of claim 1, further comprising a label, the label comprising a fluorescent dye, an enzyme, a protein tag, a fluorescent protein, or biotin.

3. The polypeptide of claim 1, wherein the polypeptide consists of the amino acid sequence of SEQ ID NO: 1 or SEQ ID NO: 3.

* * * * *